United States Patent
Mehrhof

(10) Patent No.: US 9,474,589 B2
(45) Date of Patent: Oct. 25, 2016

(54) TOOTH IMPLANT

(75) Inventor: Jurgen Mehrhof, Berlin (DE)

(73) Assignee: MEHRHOF IMPLANT TECHNOLOGIES GMBH, Berlin (DE)

(*) Notice: Subject to any disclaimer, the term of this patent is extended or adjusted under 35 U.S.C. 154(b) by 760 days.

(21) Appl. No.: 13/133,433

(22) PCT Filed: Dec. 11, 2009

(86) PCT No.: PCT/EP2009/066899
§ 371 (c)(1),
(2), (4) Date: Jun. 8, 2011

(87) PCT Pub. No.: WO2010/066871
PCT Pub. Date: Jun. 17, 2010

(65) Prior Publication Data
US 2011/0244424 A1 Oct. 6, 2011

(30) Foreign Application Priority Data

Dec. 12, 2008 (DE) .................. 10 2008 054 588
May 8, 2009 (DE) .................. 10 2009 002 947

(51) Int. Cl.
A61C 8/00 (2006.01)

(52) U.S. Cl.
CPC ............. *A61C 8/0086* (2013.01); *A61C 8/005* (2013.01); *A61C 8/0059* (2013.01)

(58) Field of Classification Search
CPC ... A61C 8/0086; A61C 8/005; A61C 8/0059
USPC ................................................. 433/172–176
See application file for complete search history.

(56) References Cited

U.S. PATENT DOCUMENTS 4,626,214 A * 12/1986 Artal .......................... 433/174
4,631,031 A * 12/1986 Richter ....................... 433/173
(Continued)

FOREIGN PATENT DOCUMENTS

CH         696625        8/2007
DE     195 09 118 A1    9/1996
(Continued)

OTHER PUBLICATIONS

International Search Report dated Apr. 13, 2010 in International Patent Application No. PCT/EP2009/066899 (2 pages).
(Continued)

*Primary Examiner* — Matthew Nelson
(74) *Attorney, Agent, or Firm* — Price Heneveld LLP

(57) ABSTRACT

The invention relates to a multi-part tooth implant with at least a proximal implant part and a distal implant part that are to be connected to each other such that a connection site is obtained when the two implant parts are in the connected state. An annular sealing element is arranged at this connection site and, in the fully assembled state of the tooth implant, is clamped between mutually opposite sealing surfaces, namely a sealing surface of the proximal implant part and a sealing surface of the distal implant part, such that the sealing element has an outer surface portion that forms part of the outer contour of the tooth implant. The two sealing surfaces initially approach each other in a direction oriented outwards from a central longitudinal axis of the tooth implant. The sealing surfaces merge into outer surfaces of the tooth implant at the place where, in the outer contour of the fully assembled tooth implant, a surface portion formed by the sealing element in each case adjoins a surface portion formed by the respective implant part. These outer surfaces move away from each other in the outwardly oriented direction.

8 Claims, 16 Drawing Sheets

(56) References Cited

U.S. PATENT DOCUMENTS

| | | | |
|---|---|---|---|
| 4,756,689 A | | 7/1988 | Lundgren et al. |
| 4,927,363 A | * | 5/1990 | Schneider ............... 433/173 |
| 4,993,950 A | * | 2/1991 | Mensor, Jr. ............ 433/173 |
| 5,040,982 A | | 8/1991 | Stefan-Dogar |
| 5,098,294 A | * | 3/1992 | Lee et al. ............... 433/169 |
| 5,695,335 A | * | 12/1997 | Haas et al. ............. 433/173 |
| 5,947,734 A | * | 9/1999 | Hanel ...................... 433/173 |
| 6,315,563 B1 | * | 11/2001 | Sager ...................... 433/173 |
| 2005/0210992 A1 | * | 9/2005 | Tohyama et al. ......... 73/715 |
| 2009/0123889 A1 | | 5/2009 | Mehrhof |

FOREIGN PATENT DOCUMENTS

| | | |
|---|---|---|
| DE | 19509118 | 9/1996 |
| DE | 19815719 | 1/2000 |
| DE | 29924510 | 9/2003 |
| DE | 202005015074 | 4/2006 |
| RU | 2187283 C2 | 8/2002 |
| WO | 2007031562 | 3/2007 |

OTHER PUBLICATIONS

English Abstract, CH 696625A, 1 page.
English Abstract, DE 198 15719 C1, 1 page.
English Abstract, DE 195 09 118 A1, 1 page.
English Abstract, DE 20 2005 015 074 U1, 1 page.
English Abstract, DE 299 24 510 U1, 1 page.
Bibliograhic data including English abstract, Document DE 195 09 118 A1, DEPATISnet, 2 pages.
Bibliograhic data including English abstract, Document RU 2187283 C2, DEPATISnet, 2 pages.

* cited by examiner

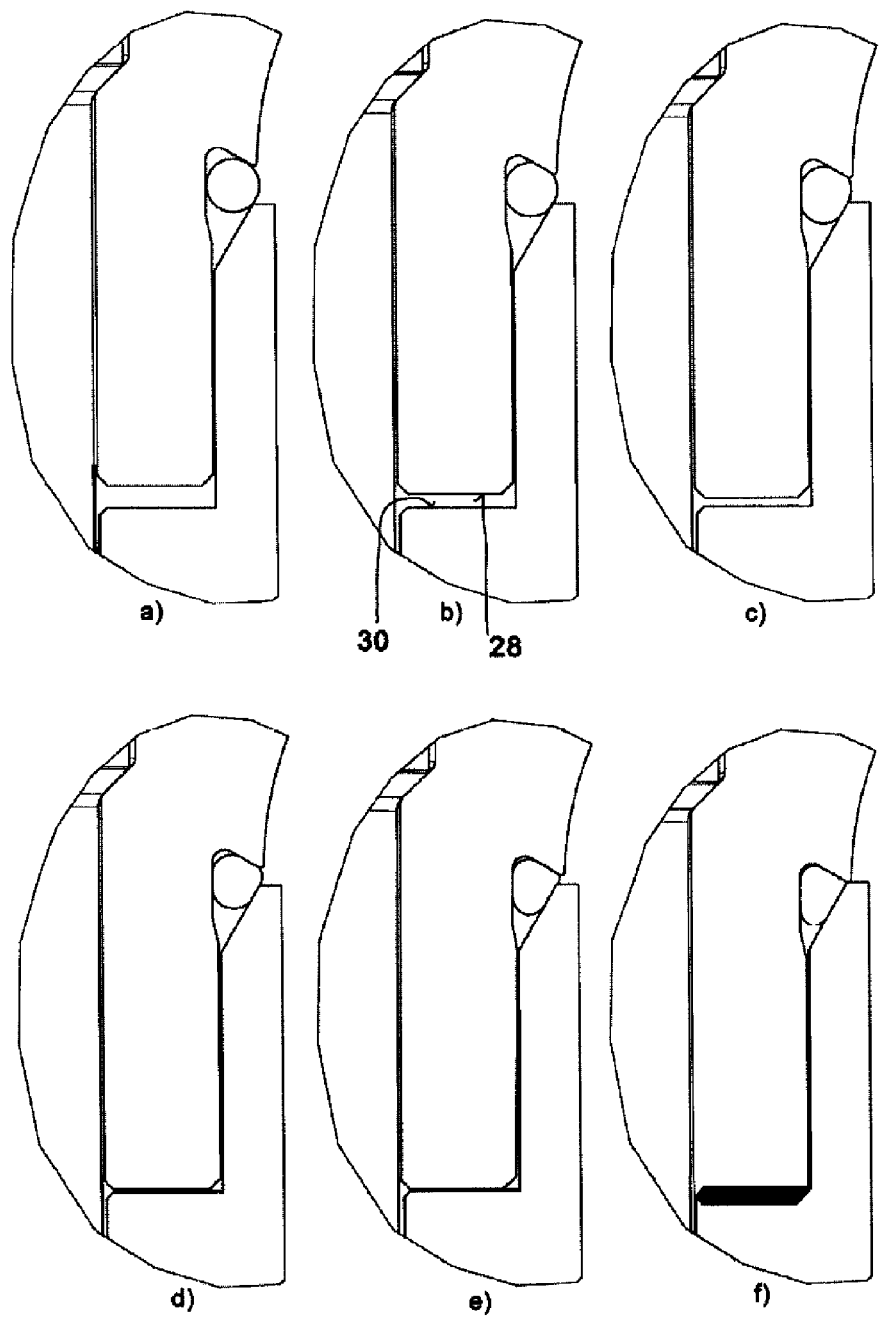
Fig. 15a-f

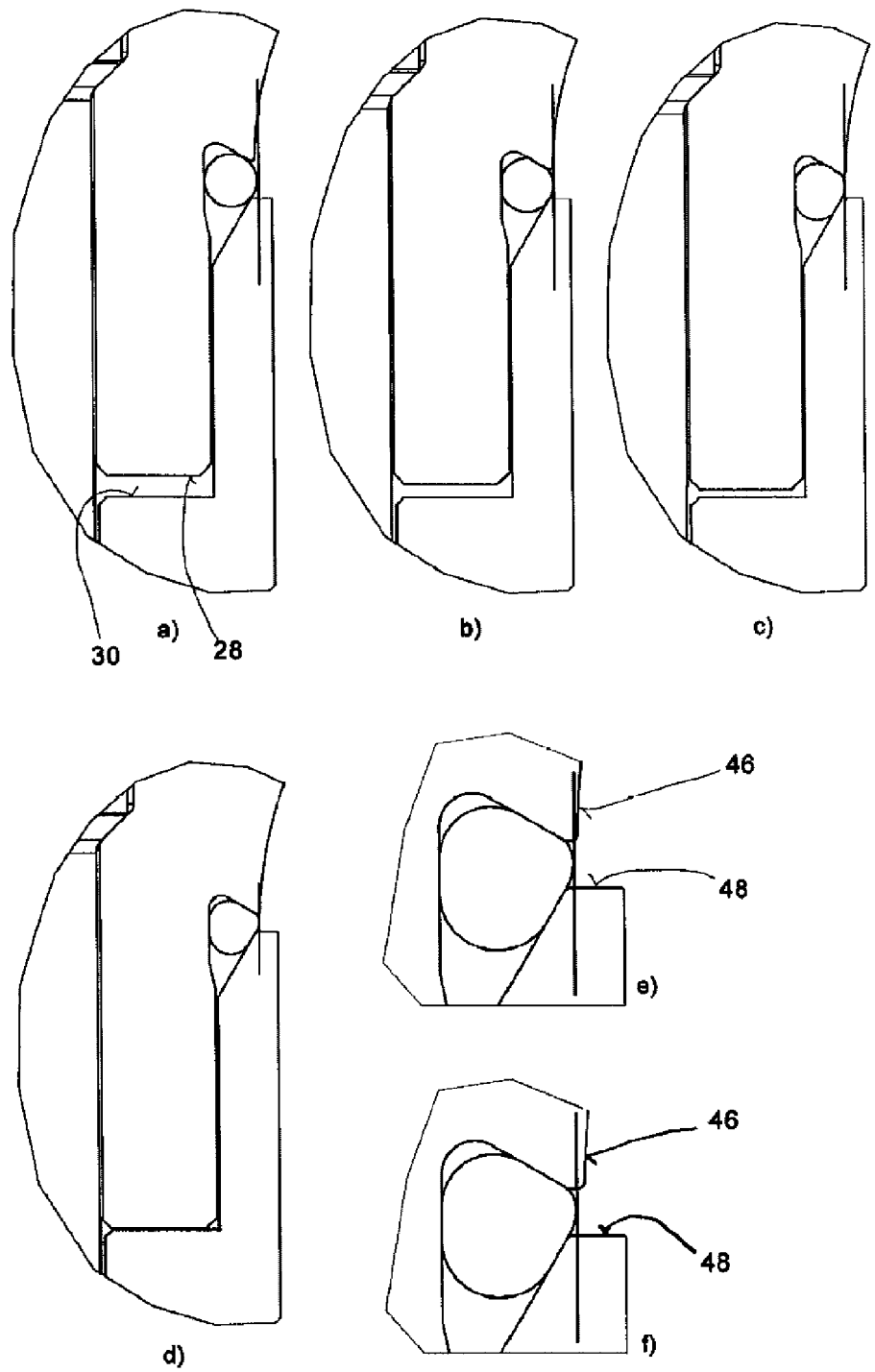
Fig. 16 a-f

TOOTH IMPLANT

BACKGROUND

The invention relates to a multi-part tooth implant with at least a proximal implant part and a distal implant part that are to be connected to each other such that a connection site is obtained when the two implant parts are in the connected state. An annular sealing element is provided between the two implant parts.

Tooth implants of this type are known, for example, from DE 20 2005 015 074, DE 299 24 510 or U.S. Pat. No. 4,756,689. In all these cases, a distal implant part serves as an artificial tooth root which can be screwed into a jawbone at the respective site prior to attaching a proximal implant part and, if necessary, further implant parts to the distal implant part. The proximal implant part usually serves as a build-up partial stem and carries an artificial tooth crown. In many cases, the distal and the proximal implant parts are connected to one another by a cylinder screw.

At the connection site between the distal and the proximal implant parts, there is the problem that, depending on the make, bacteria may enter and accumulate there more or less heavily, which might lead to inflammation, for example.

BRIEF SUMMARY

The object underlying the invention is to provide a multi-part tooth implant which, in the area of the connection site, is designed such that the known disadvantages are avoided as far as is possible.

According to the invention, this object is achieved by a tooth implant—hereinafter shortly referred to as implant—of the type mentioned at the beginning, in which the sealing element is annular and elastic and, in its fully assembled state, the tooth implant is clamped between mutually opposite sealing surfaces, viz. a sealing surface of the proximal implant part and a sealing surface of the distal implant part, such that the sealing element has an outer surface portion that forms a part of the outer contour of the tooth implant, wherein the two sealing surfaces converge in a direction oriented outwards from a central longitudinal axis of the tooth implant—i.e. they approach each other—and they merge into respective outer surfaces of the tooth implant at the place where, in the respective outer contour of the fully assembled tooth implant, a surface portion formed by the sealing element in each case adjoins a surface portion formed by the respective implant part, which outer surfaces move away from each other in the outwardly oriented direction, i.e. they diverge.

Preferably, one of the at least two implant parts comprises an outer sealing seat for the elastic, annular sealing element, which sealing seat is located outside with respect to a central longitudinal axis of the tooth implant. Said sealing seat is designed such that it is formed by at least two surface portions of this one implant part running in the circumferential direction. Said two circumferential surface portions of the one implant part enclose an angle between themselves with respect to a longitudinal cross-section through this implant part, which angle has an angle bisector with a directional component oriented radially towards the outside so that the sealing seat is open towards the outside with respect to the radial direction. The two surface portions of the implant part running in the circumferential direction are designed such that, both in a longitudinal part facing the other implant part and in the radial direction, they bear or support from the inside the annular sealing element due to the angle enclosed by them in the connected state of the two implant parts.

The other implant part has at least a surface portion running in the circumferential direction, which is arranged and designed such that it presses the sealing element into the angle in the connected state of the two implant parts.

Furthermore, the two implant parts are preferably designed such that the sealing element in the connected state of the two implant parts forms a surface portion of the outer contour of the tooth implant which, in the longitudinal direction of the tooth implant, is adjoined by respective surface portions of the proximal or distal implant part, respectively. Each of said surface portions of the one or the other implant part, in the longitudinal cross-section through the connected tooth implant, has a tangent at the place where it touches the surface portion of the sealing element forming an outer contour of the tooth implant so that two tangents result. The two outer surface portions of the implant parts adjoining the sealing element are designed such that said two tangents enclose between themselves an angle open towards the outside with respect to the implant.

As a result, the outer contour of the assembled tooth implant does not comprise any recesses or gaps in which bacteria may accumulate. Rather, the sealing element—or to be more exact: an outer surface portion of the sealing element is exposed when the tooth implant is fully assembled.

Preferably, in the connected state of the two implant parts, the elastic sealing element has a larger diameter than at least one of the two implant parts in close vicinity to the sealing element.

It is further preferred that the two implant parts comprise mutually facing abutment surfaces which abut or meet in the connected state of the two implant parts and, thus, limit the degree of compression of the elastic sealing element. In this case, said abutment surfaces are located within the outer contours of the tooth implant closed by the sealing element.

The abutment surfaces preferably each run in a surface transverse both to the longitudinal axis of the tooth implant and to a respective cross-sectional plane of the tooth implant and, thus, simultaneously serve as longitudinal abutment and as anti-twist protection.

Further details of a preferred design of the abutment surfaces can be found in publication WO 2007/031562 by the same inventor. Reference is made in particular to FIGS. 1 to 12 and the respective description of said publication.

According to this publication, it is preferred that a distal partial stem forming a distal implant part comprises a longitudinal opening open towards its proximal end with an inner wall having a basic geometry with a circular cross-section and which comprises v-shaped recesses which at least approximately extend in the longitudinal direction of the partial stem and are open towards the proximal end of the partial stem. A build-up partial stem forming a proximal implant part, at its distal end, comprises a longitudinal projection with an outer wall having a basic geometry with a circular cross-section, into which the longitudinal opening of the distal partial stem fits.

The respective sealing surfaces for the sealing element designed according to the invention enclose the longitudinal opening and the longitudinal projection, respectively, of the respective implant part.

Preferably, the outer wall of the build-up partial stem comprises, in the area of its distal end, v-shaped projections, which are adapted to the v-shaped recesses of the distal partial stem such that flank portions of the v-shaped recesses of the distal partial stem interact with flank portions of the v-shaped projections of the build-up partial stem such that the v-shaped projections of the build-up partial stem slide like a wedge into the v-shaped recesses of the distal partial stem, until two respective flanks of a v-shaped projection and two flanks of a v-shaped recess touch each other and, in this way, fix without clearance the relative position of the distal partial stem and build-up partial stem both in the axial and in the rotatory direction, when the distal partial stem and the build-up partial stem are being connected or are connected to one another. The flanks touching each other serve as abutment surfaces and form a defined height abutment. The height abutment is represented by a defined geometric form of the implant parts themselves. Thus, the forces acting from above on the proximal implant part (proximal partial stem) are transmitted only to the distal implant part (distal partial stem). If the acting forces were diverted not by the height abutment described but by a seal, said seal would be destroyed during the duration of its use.

Here, the design of the distal partial stem offers the advantage that it can also accommodate a build-up partial stem without v-shaped projections so that the partial stems connected to one another in the end are precisely fixed relative to each other in the axial direction, however not in the rotatory direction. This is particularly advantageous when the stem serves for attaching a bridge. Then, no further element is required in order to accommodate the bridge. During assembly, the doctor in charge only has to screw a single interconnected element to the implant fixations in the patient's mouth.

Preferably, the flanks of the v-shaped projections or recesses, respectively, with respect to a cross-sectional plane running perpendicular to the longitudinal axis of the implant, extend radially towards the outside and, thus, run perpendicular to the circumferential direction. Consequently, no radial forces are transmitted by the flanks which touch each other after the implant has been assembled, which forces, for example, might cause the bursting of a distal partial stem made from ceramics.

If the distal partial stem is made of a more tensile material, such as metal, in particular titanium, the flanks may also be inclined with respect to the above-described strictly radial orientation such that flanks associated with a respective projection of the build-up partial stem (i.e. the proximal implant part) or with a respective recess of the distal partial stem (distal implant part), respectively, run towards each other in the outwards direction. For example, the flanks may be inclined by 45° with respect to the radial direction and, thus, also with respect to the circumferential direction. Thus, the flanks do not only have a centering effect with respect to the direction of rotation, but also in the lateral direction.

The basic geometry of the outer wall of the build-up partial stem advantageously is conical at least in the area of the v-shaped projections. Accordingly, advantageously, also the basic geometry of the inner wall of the longitudinal opening of the distal partial stem is conical at least in the area of the v-shaped recesses.

For certain applications and, in particular, when the distal partial stem is made of ceramics, it may be advantageous when the basic geometry of the outer wall of the build-up partial stem as well as the basic geometry of the inner wall of the longitudinal opening of the distal partial stem is cylindrical at least in the area of the v-shaped recesses.

In both cases, the fit between the outer wall of the build-up partial stem and the inner wall of the distal partial stem preferably has a clearance fit at least in the area of the v-shaped recesses.

Moreover, at both the distal partial stem as well as at the build-up partial stem preferably four v-shaped recesses or v-shaped projections, respectively, are provided which are evenly distributed along the circumference of the respective partial stem. In this way, in the direction of rotation between the distal partial stem and the build-up partial stem, there are provided four exactly defined positioning options. Alternatively, it is also possible to provide more or fewer projections and recesses whose numbers correspond to each other and which preferably are evenly distributed along the circumference of the respective partial stem. Suitable numbers are, e.g., 3, 6 or 8.

It can also make sense to provide a projection with a widely opened V shape (obtuse V angle) in connection with a corresponding recess in the distal partial stem.

Possible V angles (opening angle of the respective V shape) are angles between 10° and 170°. In the sense of a self-centering embodiment it is advantageous when the V angle is smaller than the apex angle of the respective friction cone which results due to the pairing of material in the area of the mutually opposite flanks of the v-shaped projections and recesses, respectively.

Suitable materials for the sealing body are bio-compatible plastics, in particular elastomers and duromers. Among these is to be also a particularly suitable mixture of natural rubber and PTFE. Preferably, this mixture contains soot as a filler material. Also thermoplastic elastomers and elastomer alloys (e.g polypropylene from the group of the polyolefins), thermoplastic materials (e.g. perfluoro elastomers (PTFE, FKM, FFKM, FFPM) and polyetheretherketone (PEEK)) and duroplasts (amino and phenolic plastics) or a silicone may be used as an elastic plastic for the sealing body.

Of said elastomers FFKM is particularly suited, which contains as a basic material PTFE and as a filler material silica. A blackening of such an elastomer may be achieved using soot, and a whitening may be achieved using titanium dioxide or barium sulfate. Silica alone may already achieve a sufficient whitening.

Particularly suited is also a sealing body which largely is made from an elastomer coated on its outside with a thermoplastic material or a duromer, viz. preferably with PTFE. Here, the elastomer steadily maintains the tension and the PTFE is mouth-resistant and seals long-lastingly.

Another suitable coating material is a dimer such as diapraxylylene which is also known as parylene and which can be applied to surfaces to be coated in a plasma coating process. Suitable layer thicknesses are between 0.5 μm and 50 μm. Layer thicknesses between 1 μm and 5 μm, e.g. 3 μm, are particularly suitable. Exemplary structural formulae of such a coating material are shown hereinafter:

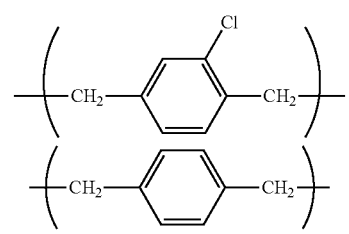

The surface of the parylene coating or also of the plastic material (sealing material itself) may additionally be provided with a nano coating of metal such as titanium or silver—also in combination with a ceramic, silicon dioxide, calcium phosphate, carbon. The coating provides both for bacteria-tightness and at the same time for neutral behavior in relation to the cell tissue.

A constituent of the sealing material may also be silver in the form of micro or nano particles.

The respective surface to be coated is preferably polarized in order to increase the adhesiveness thereof for the coating. Such a polarization of the surface may be effected in a basically known fashion by means of a plasma process.

In addition, it may be advantageous for surfaces of the implant or its constituent parts, in particular the outwardly oriented surface of the sealing body, to be polarized in order to achieve better body compatibility. Polarization provides that the adjoining tissue, such as for example bone and gums, do not or cannot demonstrate rejection behavior in relation to the coating.

In regard to a possibly partially coated sealing body it makes sense if the coated surfaces do not have any sharp edges. Rather, all coated edges should be rounded in order to prevent the coating from flaking off upon deformation of the sealing body.

It is advantageous if the elastic material of the sealing body is elastically stretchable or compressible by at least 5%, better by more than 20%. In an embodiment, by way of example, the spacing, which is predetermined by the abutment surfaces, between the mutually facing surfaces of the two implant parts is 250 μm so that the seal has a nominal dimension of 250 μm. In this case, the sealing body should be made for example 50 μm over the nominal dimension (250 μm) of the seal so that after assembly a compression of 50 μm (20% compression) already occurs. Those values represent an ideal dimension that it is sought to achieve. The structural height of the seal should be as small as possible in order for aesthetic reasons not to give away structural height for the later tooth crown; in particular dimensions between 0.1 mm and 3 mm are considered as the nominal dimension. In terms of dimensioning, it is crucial that the seal, even under the effect of mastication forces, is deformed only in the range of the elastic deformability thereof and also always remains compressed by a minimum amount in partial regions, e.g. in the event of a lateral loading. Thus, when the implant is assembled, the sealing body is compressed only by the necessary degree so that the implant-abutment connection ensures sealing integrity under all possible circumstances. The degree of compression is dependent on the material and the thickness of the material, when using a greater structural height for the seal, the compressibility of the material might be less in order to compensate for the movements in the sealing region.

For a sealing body which expands when heat is involved in particular plastic materials with a high coefficient of thermal expansion of more than 75×10-6/K at 20° C. are advantageous.

Preferably, at least one outside surface of the sealing body, which surface forms the outside surface of the implant, is coated with a metal or ceramic layer in the manner described hereinbefore, wherein the metal-parylene or ceramic layer prevents bacteria from penetrating into seal components which are covered by the metal or ceramic layer. A nano coating, for example with titanium particles, is particularly suitable. The sealing surface itself may directly consist of a biocompatible plastic material or may be coated in the above-mentioned manner. In particular titanium, silver or gold, possibly also in the form of a constituent of an alloy, are considered as the material for the metal layer. All surface materials of the seals are mouth-resistant and sterilizable and do not absorb water or absorb water only to a very slight degree.

Besides elastic plastic material the sealing body may also contain a metal spring or a separate plastic spring element of another plastic material, such as for example PEEK. The spring element can be in the form, for example, of a plate spring or a ring of a u-shaped, inwardly open cross-section and ensures permanent elasticity and stressing force for the sealing body. A metal spring may be advantageous in particular in relation to a sealing body in which the elastic plastic material at least partially is made of polytetrafluoroethylene (PTFE, Teflon), polypropylene (PP) or also polyetheretherketone (PEEK).

BRIEF DESCRIPTION OF THE DRAWINGS

The invention is now described in more detail with the help of embodiments and referring to the Figures. The Figures show:

FIG. 1a: a cross-sectional view of a first variant of a two-part tooth implant;

FIG. 1b: an enlargement of a section of FIG. 1a;

FIG. 2a: a cross-sectional view of a second variant of a two-part tooth implant with a compacted sealing ring;

FIG. 2b: an enlargement of a section of the sealing seat of the tooth implant from FIG. 2a;

FIG. 4a: the two-part tooth implant from FIG. 2 and the not yet compacted sealing ring in longitudinal cross-section;

FIG. 4b: an enlargement of a section from FIG. 4a;

FIG. 6a: a third variant of a two-part tooth implant in longitudinal cross-section;

FIG. 6b: an enlargement of a section from FIG. 6a;

FIG. 8a: a fourth variant of a two-part tooth implant in longitudinal cross-section;

FIG. 8b: an enlargement of a section from FIG. 8a;

FIG. 10a: a sixth variant of a two-part tooth implant in longitudinal cross-section;

FIG. 10b: an enlargement of a section of the sealing seat from FIG. 10a;

FIGS. 15a to 15f: a view of the stepwise deformation of the sealing ring when assembling the two-part tooth implant according to FIGS. 11 to 14, FIG. 15f shows a state that is not possible;

FIGS. 16a to 16f: different representations in order to explain the outer contour of a two-part tooth implant according to FIGS. 11 to 15 during and after the assembly of the two implant parts.

DETAILED DESCRIPTION

Figure 1:
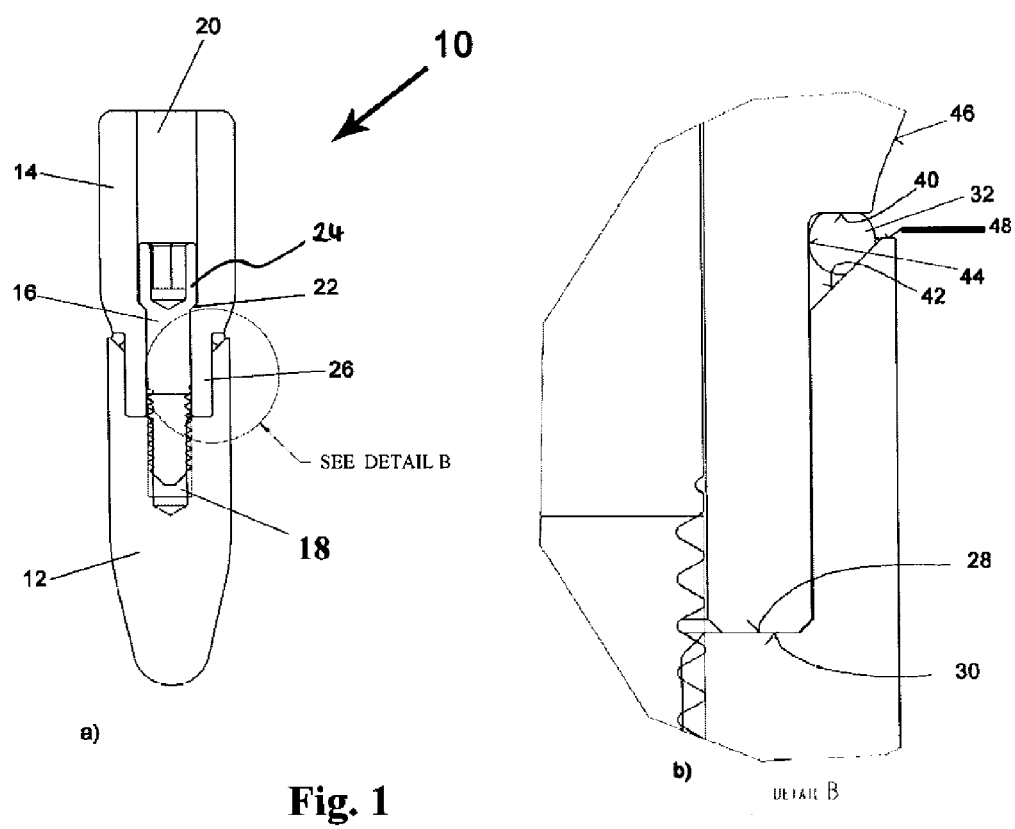

FIG. 1 shows a first variant of a two-part tooth implant 10. The two-part tooth implant comprises a distant implant part 12, also referred to as distal partial stem, which forms an artificial root of the tooth implant 10 and, therefore, is also referred to a root partial stem.

Moreover, the tooth implant 10 comprises a proximal implant part 14, which is also referred to as proximal partial stem or build-up partial stem. The proximal implant part 14 serves for accommodating an artificial tooth crown (not shown).

As can be seen in FIG. 1a, the distal implant part 12 and the proximal implant 14 are connected to one another in the fully assembled state by means of a stud bolt 16. To this end, there is provided in the distal implant part 12 a blind hole 18 with an internal thread. The blind hole 18 runs along a central longitudinal axis of the distal implant part 12.

In the proximal implant part 14, there is provided a stepped longitudinal bore 20 along a longitudinal axis of the proximal implant part 14. The stepped longitudinal bore 20, at its proximal end, has a larger diameter than at its distal end so that a step in the inner contour of the central longitudinal bore 20 of the proximal implant part 14 results. At this step 22, a collar of a head 24 of the stud bolt 16 may be supported so that the distal implant part 12 and the proximal implant part 14 may be connected to one another in a known manner with the help of a stud bolt.

A proximal end of the central blind hole 18 in the distal implant part 12 is adjoined by a longitudinal opening having an enlarged inner diameter in the distal implant part 12. Said longitudinal opening with an enlarged diameter serves for accommodating a distal portion 26 of the proximal implant part 14. An abutting face 28 of the distal longitudinal portion 26 of the proximal implant part 14 abuts or meets a floor 30 of the longitudinal opening with an enlarged diameter in the distal implant part 12 when the tooth implant 10 is fully assembled. Thus, this floor 30 forms a longitudinal abutment for the approach between the distal implant part and the proximal implant part 14 during assembly, which is done by screwing the stud bolt 16.

It has to be noted that said longitudinal abutment is virtually located inside the fully assembled tooth implant 10. The outer contour of the fully assembled tooth implant 10 is bridged between the outer contour of the distal implant part 12 and the outer contour of the proximal implant part 14 by a sealing element 32, also referred to as sealing body. The sealing element 32 has the form of an O ring with round cross-section. Instead of a round cross-section, the sealing element 32 could also have an oval cross-section.

The sealing element 32 is, in the assembled state of the tooth implant 10, as is shown in FIGS. 1a and 1b, restrictedly compressed and has a correspondingly formed cross-section. In order to allow for such a deformation the sealing element 32, either entirely or partly, is made of an elastic material.

The compression and deformation of the sealing element 32 is limited by the longitudinal abutment formed, on the one hand, by the floor of the proximal longitudinal opening in the distal implant part 12 and, on the other hand, by the end face 28 of the distal longitudinal portion of the proximal implant part 14. This makes it possible for the assembled tooth implant 10 to deform elastically under bending loads without holes or gaps forming in the outer contour of the assembled tooth implant 10. In the case of such bending loads, the load is exerted on the sealing element 32 on one side of the tooth implant 10, the sealing element 32 is further compressed, and the load is relieved on the opposite outer side of the tooth implant 10, and due to its pre-compressed state it may expand elastically. In this way, it is reliably prevented that a gap forms in the area of the outer contour of the two-part tooth implant 10.

Besides, what has been said above also applies to all variants of the two-part tooth implant according to the invention, which are described hereinafter, so that it is not necessary to repeat this description for the variants described hereinafter, and the Figures depicting the variants described hereinafter use the same reference signs as have been used for the first variant of the two-part tooth implant according to FIGS. 1 to 3.

The various variants of the two-part tooth-implant shown in this Figure and the subsequent Figures differ with respect to the actual design of the respective sealing seat for the respective sealing element 32.

A common feature of all variants described hereinafter is that the respective sealing seat is formed by at least two respective surface portions running in the circumferential direction of the implant, which surface portions enclose between themselves an angle into which the respective sealing element is pressed by a circumferential edge or a circumferential surface portion of the respective other implant part when the implant is fully assembled.

The sealing element and the circumferential surface portions forming the respective sealing seat are each dimensioned and adapted to each other such that the sealing element forms a part of the outer contour of the implant when it is fully assembled. The respective outer contour of the fully assembled implant adjoining the sealing element is formed by the outer surfaces of the tooth implant, which surfaces move away from each other with respect to a direction oriented radially outwards. The proximal implant part and the distal implant part each form one of these outer surfaces which move away from each other.

The different variants of a tooth implant according to the invention, which will be described in more detail hereinafter, differ in the actual design of the respective sealing seat. In all variants, the respective sealing element 32 is designed between clamping sealing surfaces such that said surfaces approach each other in a direction oriented radially outwards with respect to the fully assembled tooth implant. One of the sealing surface, hereinafter also referred to as proximal sealing surface 40, is formed by the proximal implant part 14, while the opposite of the two sealing surfaces is hereinafter also referred to as distal sealing surface 42 and formed by the distal implant part 12. Moreover, the sealing seat is defined by a supporting surface 42 which, in the embodiments shown, also forms part of the proximal implant part 14. The proximal sealing surface 40 and the distal sealing surface 42 each merge into a proximal outer surface 46 and a distal outer surface 48, respectively, which move away from each other with respect to a direction oriented radially outwards. In this way, it is ensured that at the connection site between the proximal implant part 14 and the distal implant part 12 no gussets form, in which, for example, bacteria might accumulate.

As has already been mentioned, the variants described in more detail hereinafter differ in that the sealing seat formed by the respective proximal sealing surface 40, the respective distal sealing surface 42 and the respective supporting surface 44 is designed differently. In the embodiment according to FIG. 1, the proximal sealing surface 40 runs in a plane perpendicular to the longitudinal axis of the tooth implant 10, while the supporting surface 44 directly adjoins the proximal sealing surface 40 and has the form of a cylinder outer surface. The distal sealing surface 42 formed by a part of an end face of the distal implant part 12 has the form of a portion of a cone inner surface, wherein the virtual cone has a longitudinal or symmetrical axis which coincides with the longitudinal axis of the two-part tooth implant 10. In this way, the proximal sealing surface 40, the distal sealing surface 42 and the supporting surface 44 enclose a gusset between themselves, into which the compressed sealing element 32 is securely clamped in the assembled state of the two-part tooth implant. According to the invention, the gusset enclosed by the proximal sealing surface 40, the distal sealing surface 42 and the supporting surface 44 is open towards the outside in the assembled state of the tooth implant so that the outer contour of the fully assembled tooth implant 10 is bridged by an outer surface of the compressed (compacted) sealing element 32.

Figure 2:
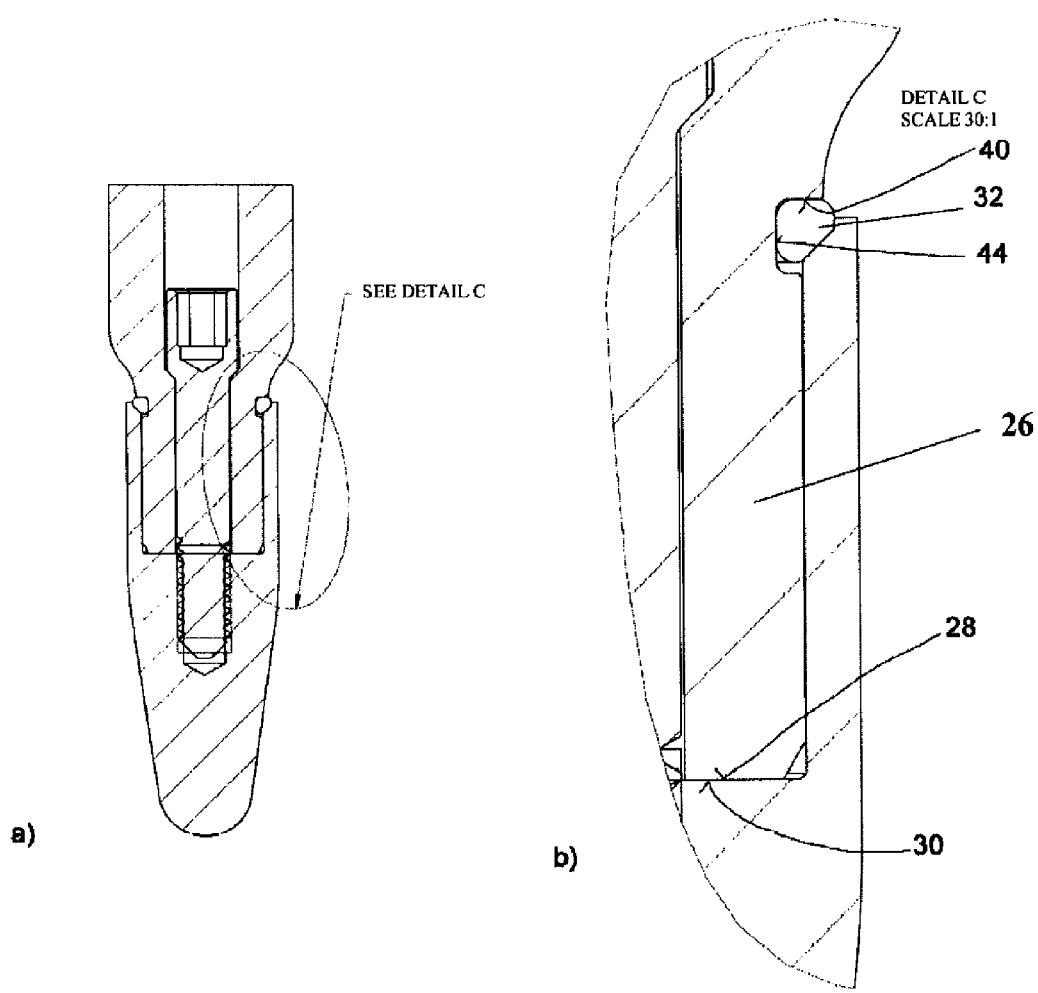
Figure 3:
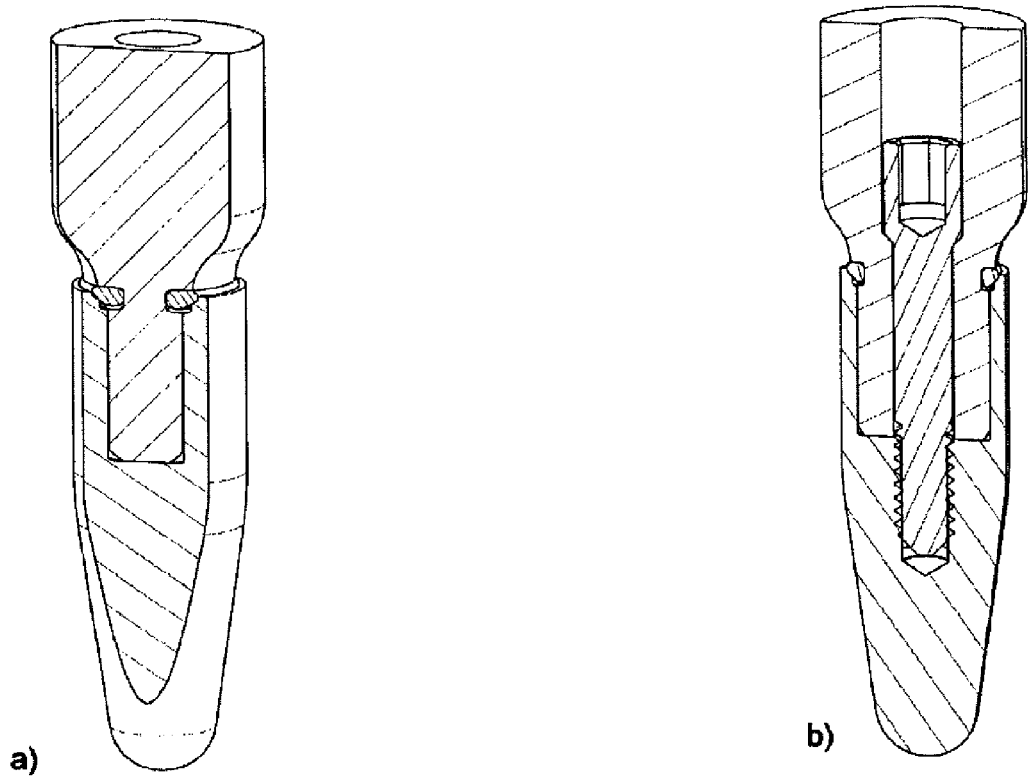
FIGS. 3a and 3b: partial cross-sectional perspective views of the tooth implant from FIGS. 2a and 2b.
Figure 4:
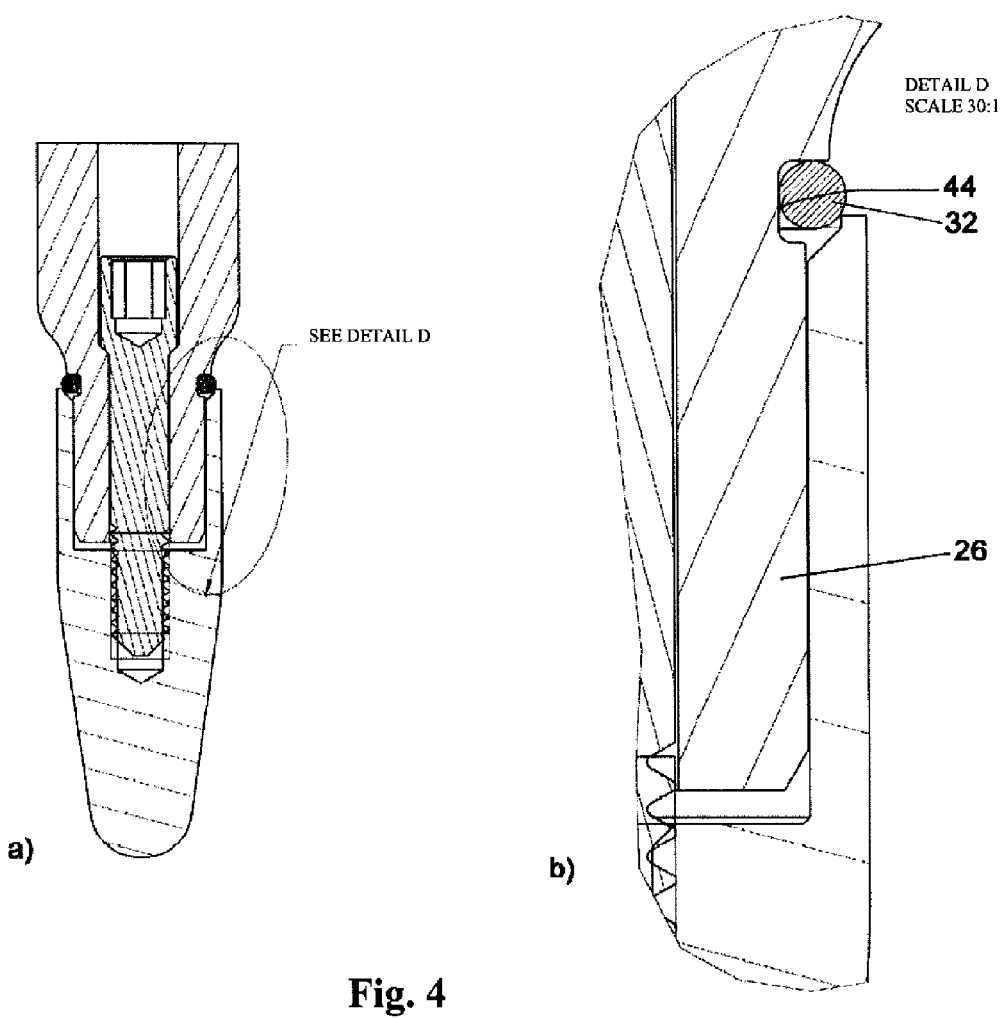
Figure 5:
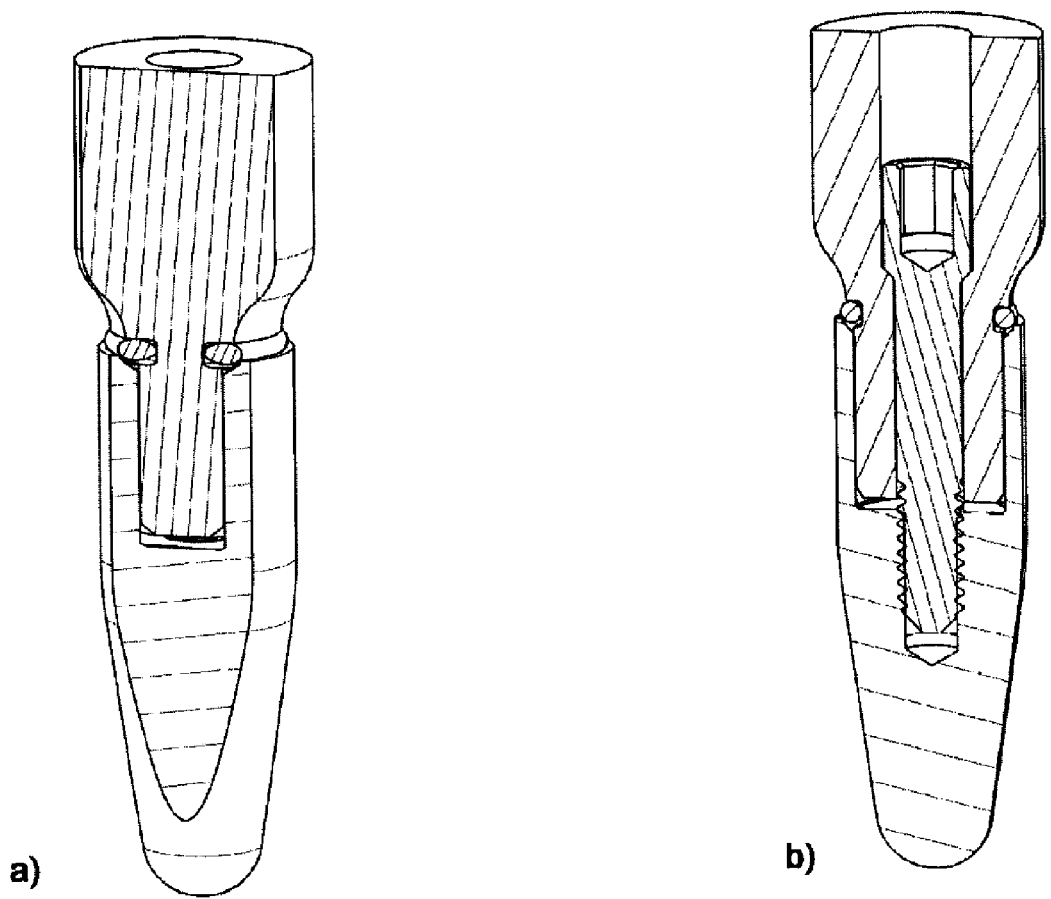
FIGS. 5a and 5b: perspective cross-sectional views of the tooth implant from FIGS. 4a and 4b.

The second variant of a two-part tooth implant shown in FIGS. 2 to 5 differs from the first variant shown in FIG. 1 only in that the supporting surface 44 does not smoothly merge into the remaining outer contour of the distal portion 26 of the proximal implant part 14, but has a smaller diameter with respect to this remaining outer contour so that a kind of a radial groove forms into which the sealing element 32 is inserted. As to the rest, the second variant of the tooth implant is essentially identical to the first variant of the tooth implant. It should be noted that FIGS. 2, 3a and 3b each show the fully assembled state of the second variant of the two-part tooth implant, each with the compressed, compacted sealing element 32, while FIGS. 4a, 4b, 5a and 5b show a state of the second variant of the two-part tooth implant, in which the end face 28 of the distal longitudinal portion of the proximal implant part 14 has not yet butted against the respective floor 30 of the longitudinal opening having an enlarged diameter in the distal implant part 12 so that the longitudinal or height abutment between the proximal implant part 14 and the distal implant part 12 has not yet become effective. To put it differently: In FIGS. 4 and 5, the proximal implant part 14 and the distal implant part 12 are not yet fully assembled. Rather, these Figures show a state in which the sealing element 32 has not yet been compressed and, hence, is still uncompacted.

Figure 6:
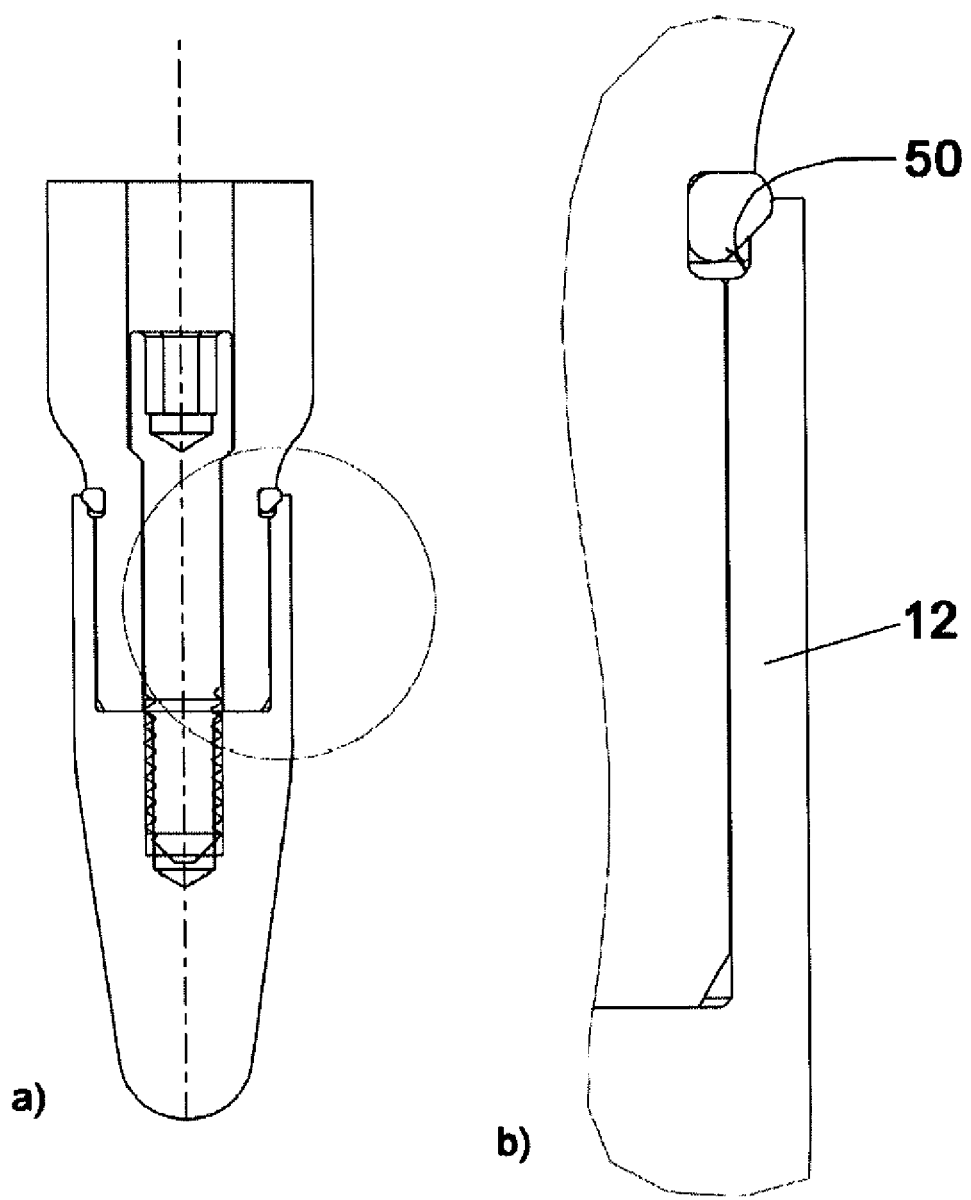

The third variant of a two-part tooth implant shown in FIG. 6 differs from the second variant shown in FIG. 2 in that the distal sealing surface 42 is formed with a smaller surface in comparison, as can be taken from FIG. 6. This is due to a respective recess 50 in the area of the proximal end of the distal implant part 12.

Figure 7:
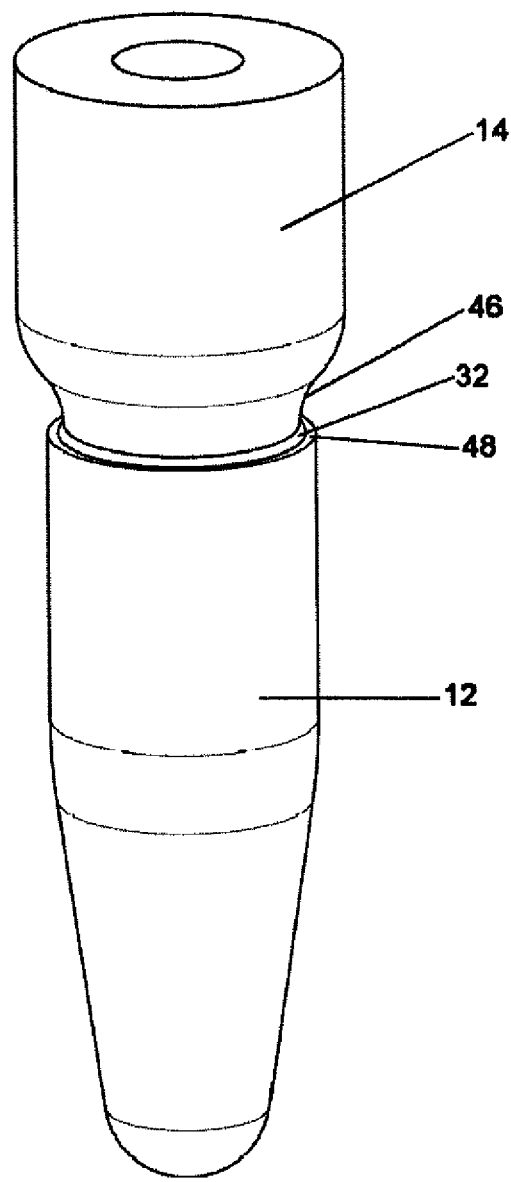
FIG. 7: a perspective outside view of a fully assembled two-part tooth implant according to the invention.

Finally, FIG. 7 illustrates that aspect of the invention according to which the sealing element 32 in the fully assembled state of the two-part tooth implant forms a part of the outer contour thereof and is arranged between two outer surfaces 46 and 48 of the two-part tooth implant, which move away from each other in a direction oriented radially towards the outside. Consequently, there is an offset between the proximal implant part 14 (build-up) and the distal implant part 12 (also referred to as implant). As can be seen, the proximal implant part 14, in the area of the connection between the proximal and the distal implant parts, has a smaller diameter than the distal implant part 12. Alternatively, the proximal implant part 14 and the distal implant part 12 could also be designed such that the proximal implant part 14, in the area of the connection between the implant parts, has a larger diameter than the distal implant part 12. This variant is not shown in the Figures.

Figure 8:
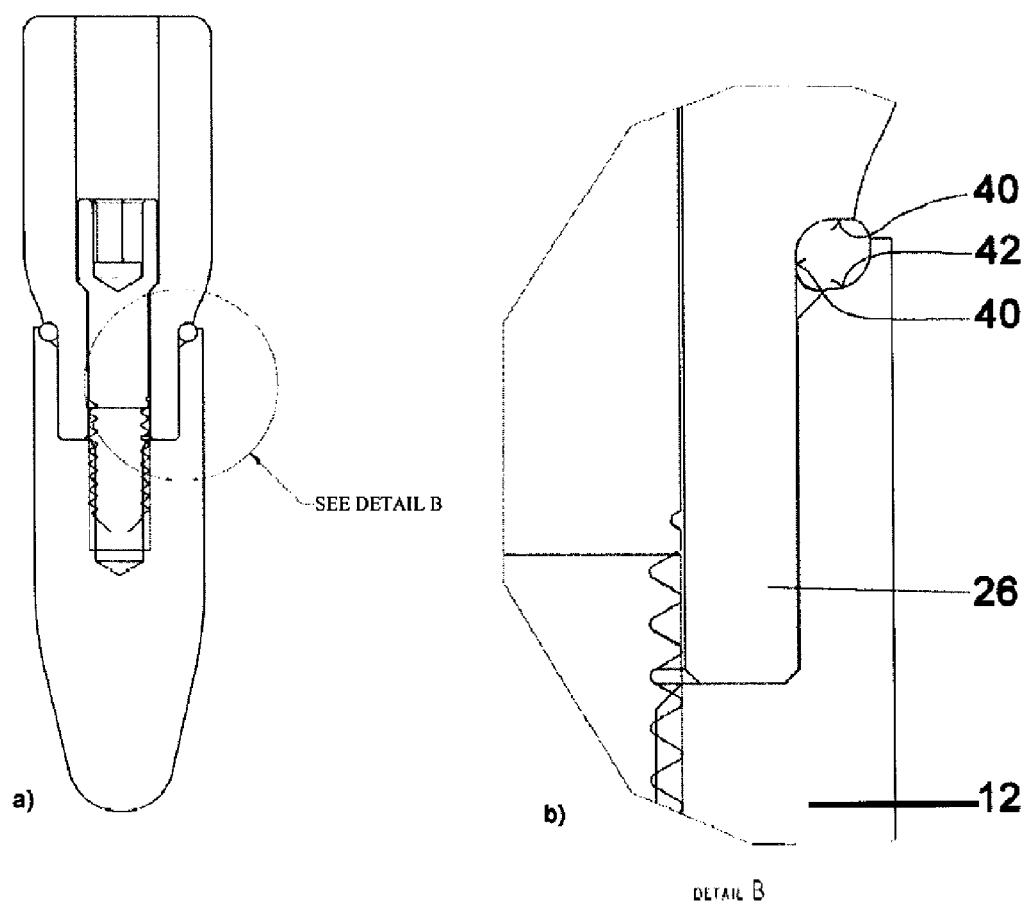

Finally, FIG. 8 shows a fourth variant of a two-part tooth implant, in which the proximal sealing surface 40 and the supporting surface 44 are designed as in the first variant. In contrast to the variants described before, the distal sealing surface 42, however, does not have the form of a cylinder inner surface, but rather the form of a hollow groove which opens transversely in the proximal direction and an inwards oriented direction. The hollow groove forms the distal sealing surface 42 and, at the same time, a room accommodating the sealing ring. The hollow groove is designed concave.

Figure 9:
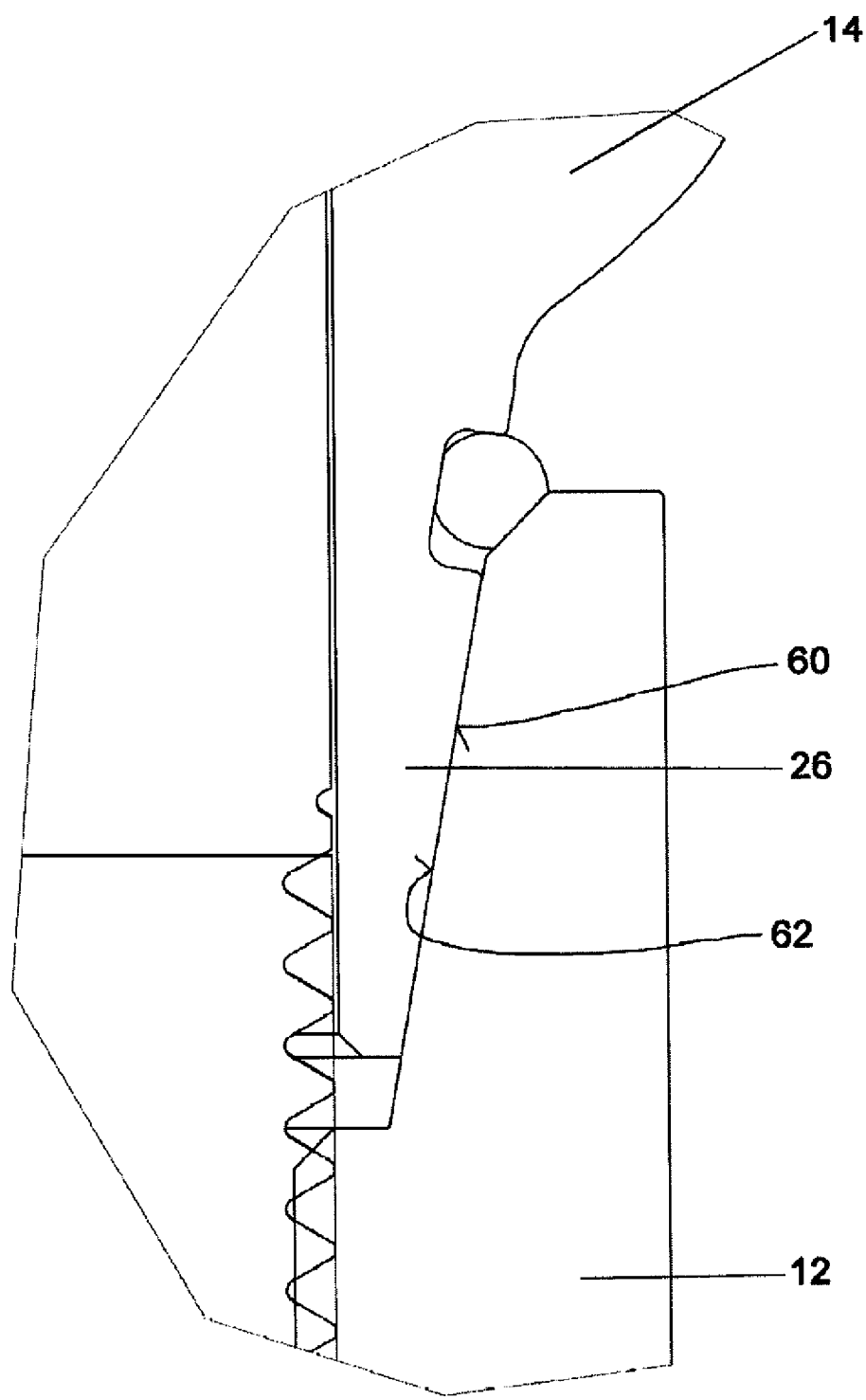
FIG. 9: the sealing seat according to a fifth variant of a two-part tooth implant in an enlargement of a corresponding longitudinal cross-section.

Finally, FIG. 9 shows a fifth variant of a two-part tooth implant, which in some respects is quite similar to the two-part variant of the tooth implant shown in FIGS. 2 to 5. An essential difference to that variant is that the distal longitudinal portion 26 of the proximal implant part 14 is not cylinder-shaped, but is designed to taper conically in the distal direction. The supporting surface 44 of the fifth variant of the tooth implant is formed by a floor of a circumferential groove which is open towards the outside and serves to accommodate the sealing element 32, and it does not have the form of a cylinder barrel portion, but the form of a cone surface portion. Alternatively, the proximal sealing surface 40 and the annular groove forming the supporting surface 44 could also be designed such that the supporting surface 44 has the form of a cylinder barrel portion and the proximal sealing surface 40 is located in a plane perpendicular to the longitudinal axis of the tooth implant.

Figure 10:
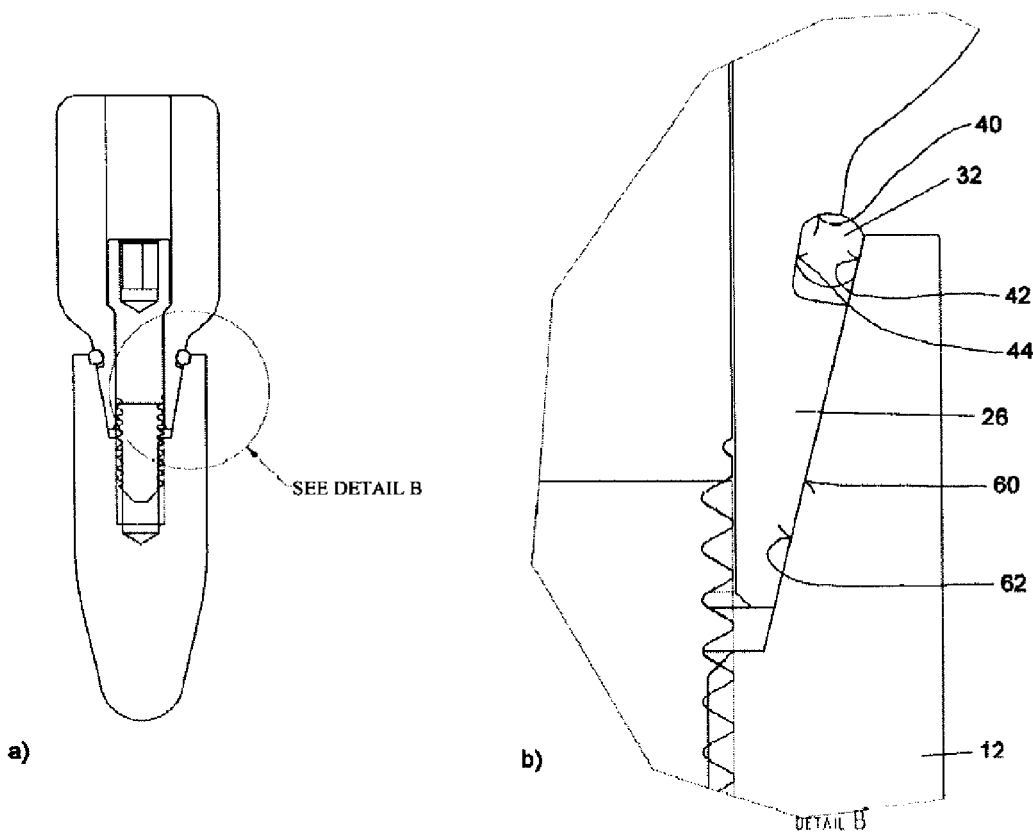
Figure 11:
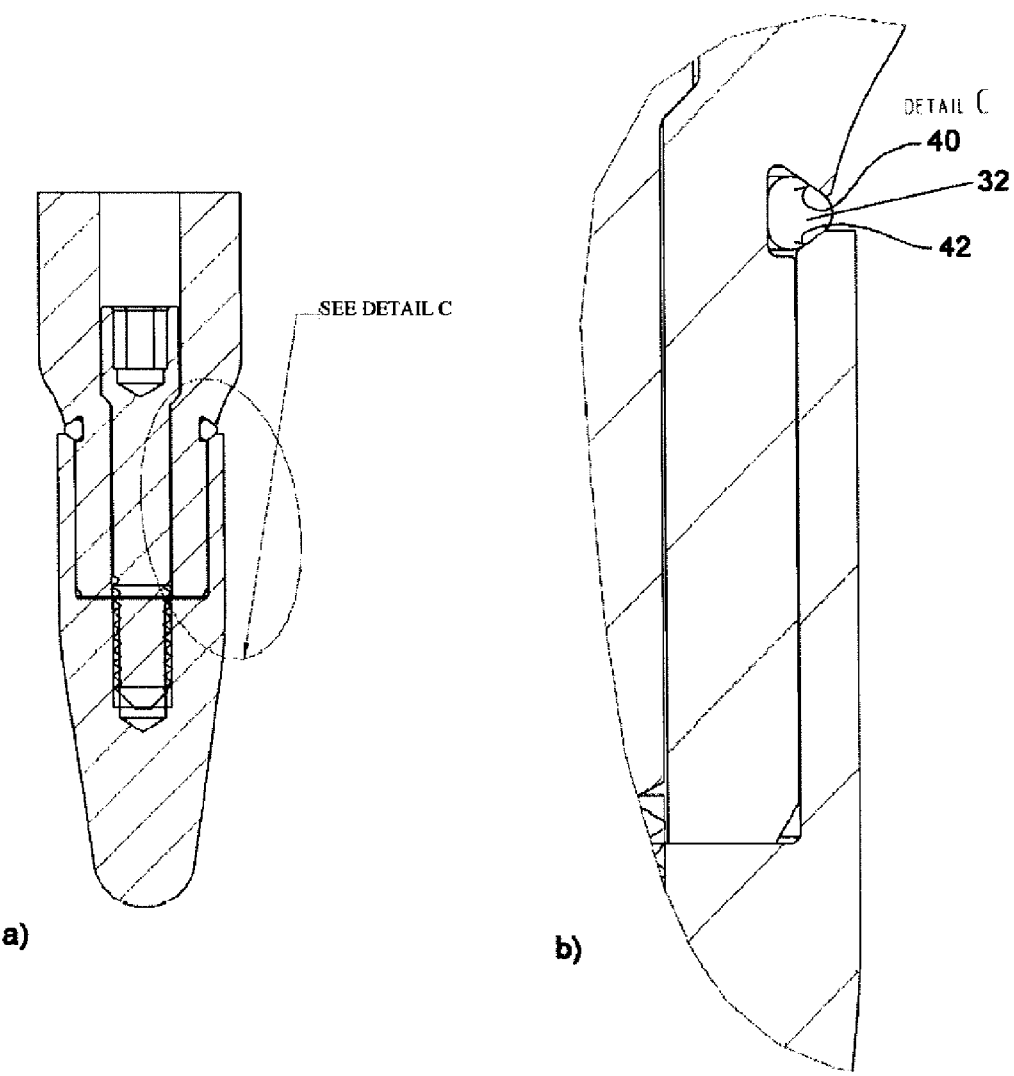
FIG. 11a: a seventh variant of a two-part tooth implant according to the invention in longitudinal cross-section.
FIG. 11b: an enlargement of a section from FIG. 11 for depicting the sealing seat.
Figure 12:
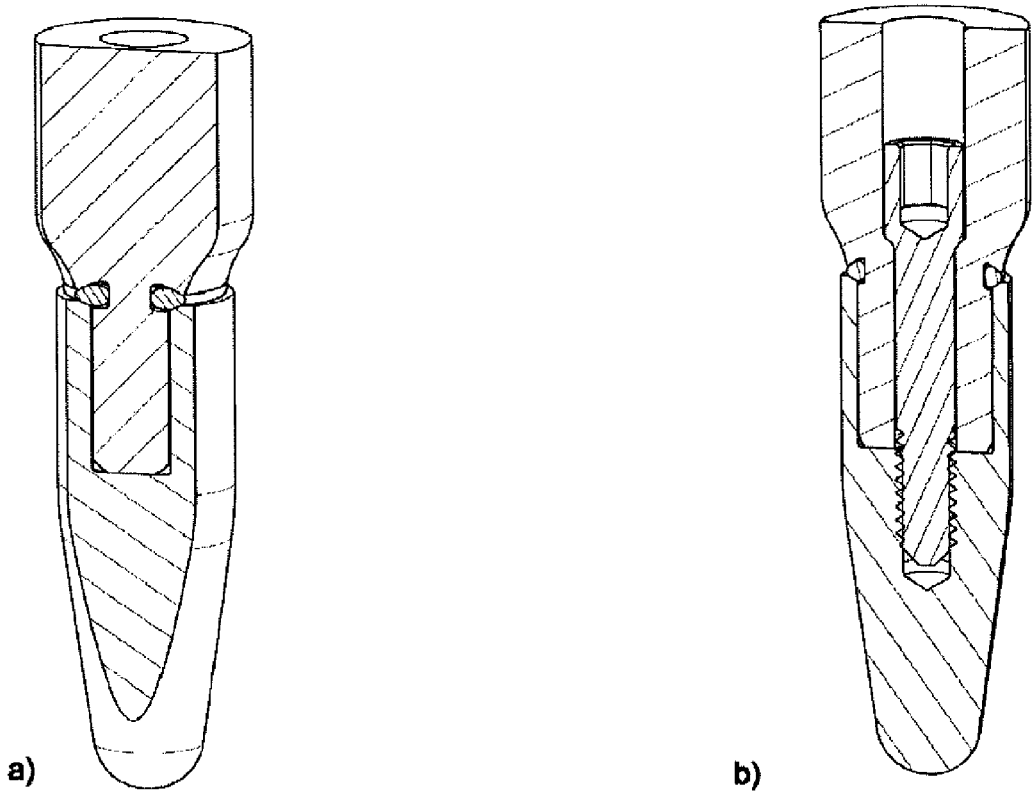
FIGS. 12a and 12b: perspective, partial cross-sectional views of the tooth implant according to FIGS. 11a and 11b.
Figure 13:
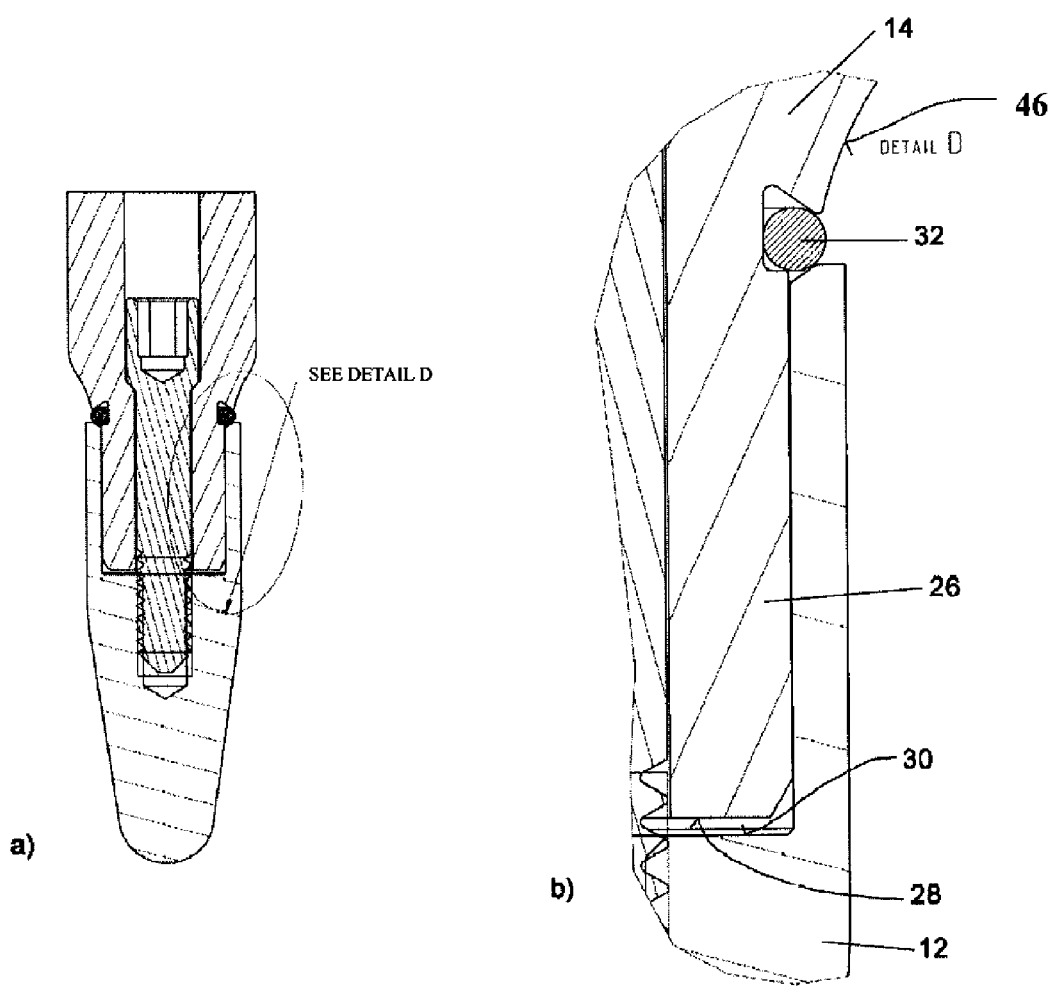
FIGS. 13a and 13b: the two-part tooth implant according to FIGS. 11 and 12 in a view with uncompacted sealing ring.
Figure 14:
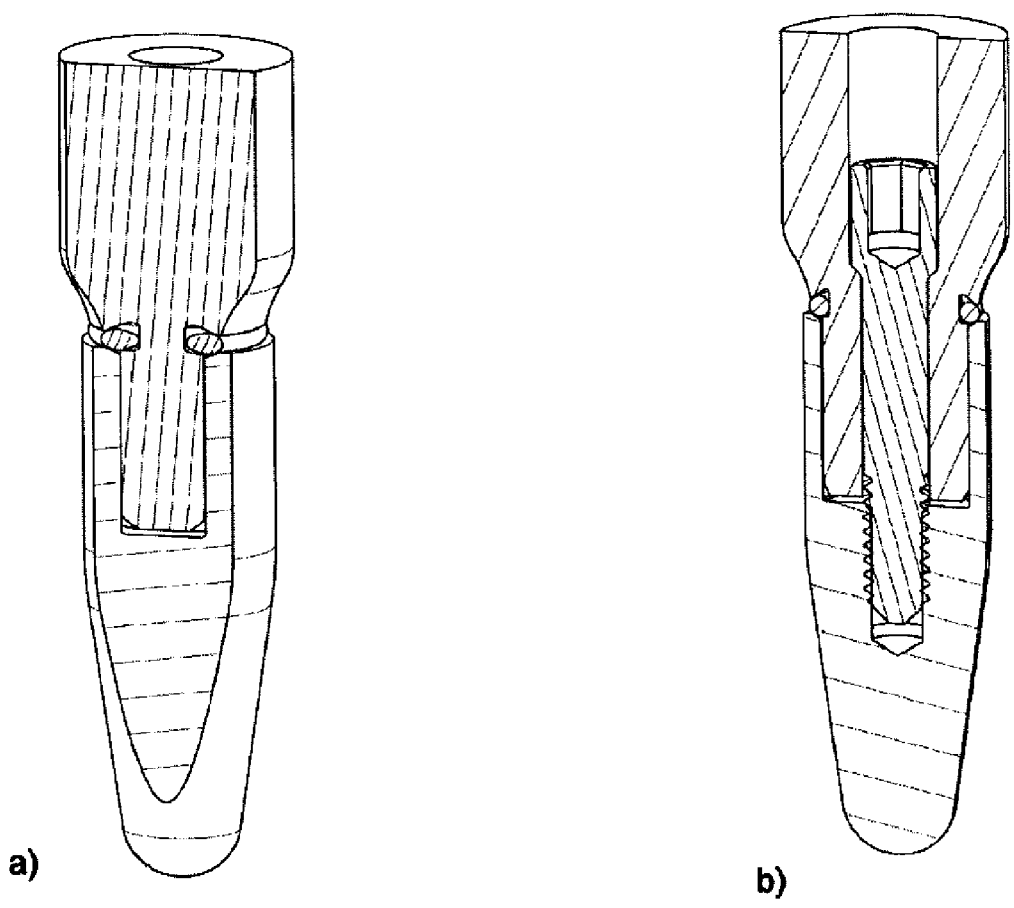
FIGS. 14a and 14b: a partial cross-sectional, perspective view of the tooth implant according to FIGS. 11 to 13 with the not yet compacted sealing ring.

A particularity of the fifth embodiment according to FIGS. 9 and 10 is that due to the conical surface 60 of the distal longitudinal portion 26 of the proximal implant part 14 as well of the corresponding opposite inner surface 42 of the implant part 14, which surface is also designed conically inside, said conical surfaces themselves form the longitudinal abutment limiting the compression of the sealing element 32.

Finally, FIGS. 11 to 14 show a seventh embodiment of the two-part tooth implant which differs from the second embodiment in particular in that the proximal sealing surface 40 runs transversely in the longitudinal cross-section and, similar to the distal sealing surface 42, has the form of a longitudinal portion of the inner surface of a hollow cone so that a trapezoidal sealing seat is formed. FIGS. 11a and 11b as well as 12a and 12b each show different views of the two-part tooth implant in the fully assembled state with the compressed compacted sealing element 32. FIGS. 14a and 14b show details of the seventh embodiment of the two-part tooth implant in a state in which the proximal implant part 14 and the distal implant part 12 are not yet fully assembled so that the opposite abutment surfaces have not yet met. The sealing element 32 is still uncompressed.

FIGS. 15a to 15f explain the effectiveness of the longitudinal or height abutment, respectively, between the end face 28 of the distal longitudinal portion 26 of the proximal implant part 14 and the floor 30 of the longitudinal opening having an enlarged diameter in the distal implant part 12. FIGS. 15a to 15d show how said opposite surfaces approach each other stepwise when both implant parts are assembled so that the sealing element 32 is further compressed until both surfaces meet, which is the final state of the fully assembled two-part tooth implant, which state is shown in FIG. 15e.

Finally, FIG. 15f shows a state which is not possible for the two-part tooth implant since the end face 28 and the floor 30—unlike what is shown virtually in FIG. 15f—cannot penetrate each other. Due to the longitudinal abutment formed by the end face 28 in the floor 30 it is also ensured that the sealing element 32 is compressed only to a limited extent and always forms a part of the outer contour of the tooth implant, as can be taken from FIG. 15 in particular.

FIG. 16 also shows how the two implant parts approach each other stepwise during assembly, until they reach the state shown in FIG. 16*d*. The details in FIGS. 16*e* and 16*f* explain variants of a conceivable outer contour of the fully assembled two-part tooth implant in the area of the connection site between the proximal implant part and the distal implant part. In particular, the details in FIGS. 16*e* and 16*f* show that an outer surface of the sealing element 32 is offset backwards only slightly—if at all—with respect to the adjoining outer surfaces of the proximal and distal implant parts so that no gaps or gussets form which cannot be reached during tooth-brushing or in which bacteria may be accommodated permanently.

The invention claimed is:

1. A multi-part tooth implant with at least a proximal implant part and a distal implant part that are to be connected to each other such that a connection portion is obtained when the two implant parts are in the connected state, wherein an annular sealing element is arranged at this connection portion, which, in the fully assembled state of the tooth implant, is clamped between mutually opposite sealing surfaces, namely a sealing surface of the proximal implant part and a sealing surface of the distal implant part, such that the sealing element has an outer surface portion that forms part of the outer contour of the tooth implant, wherein the two sealing surfaces approach each other in a direction oriented outwards from a central longitudinal axis of the tooth implant, the two sealing surfaces merge into respective outer surfaces of the tooth implant at the place where, in the outer contour of the fully assembled tooth implant, a surface portion formed by the sealing element in each case adjoins a surface portion formed by the respective implant part, which outer surfaces move away from each other in the outwardly oriented direction, characterized in that both implant parts have abutment surfaces facing the respective other implant part, which abutment surfaces abut or meet when the tooth implant is fully assembled and which define the degree of compression of the sealing element in the connected state of the tooth implant.

2. The multi-part tooth implant of claim 1, characterized in that, with respect to a central longitudinal axis, the one implant part has an outer sealing seat for the sealing element, which sealing seat is formed by at least two surface portions of said implant part running in the circumferential direction, which with respect to a longitudinal cross-section through this implant part enclose an angle between themselves which has an angle bisector with a directional component oriented radially towards the outside so that the sealing seat is open towards the outside in the radial direction, and which, in the connected state of the two implant parts, in a longitudinal direction facing the other implant part and in the radial direction, bear or support from the inside the annular sealing element due to said angle, and the other implant part has a surface portion running in the circumferential direction, which surface portion, in the connected state of the two implant parts, presses the sealing element into said angle, wherein a surface portion of the sealing element forms an outer part of the outer contour of the tooth implant in the connected state and the two outer surface portions of the implant parts adjoining the sealing element are designed such that the exposed surface portion of the sealing element forms a part of the outer surface contour of the fully assembled tooth implant which is freely accessible from the outside.

3. The multi-part tooth implant of claim 2, characterized in that, at the exposed surface portion of the sealing element in the longitudinal direction of the tooth implant, a respective surface portion of the proximal and distal implant parts, respectively, adjoins, wherein, in the longitudinal cross-section through the connected tooth implant, each of said surface portions of the one or the other implant part at the place where it touches the surface portion of the sealing element forming an outer contour of the tooth implant has a tangent so that two tangents result, and wherein the two outer surface portions of the implant parts adjoining the sealing element are designed such that said two tangents enclose between themselves an angle open towards the outside with respect to the implant.

4. The implant of claim 1, characterized in that the largest diameter of the surface portion of the sealing element forming an outer contour of the tooth implant at least approximately corresponds to or exceeds the diameter of a circumferential wall adjoining said surface portion of at least one of the implant parts.

5. The implant of claim 1, characterized in that the abutment surfaces run transversely both with respect to a longitudinal plane and with respect to a cross-sectional plane of the implant parts.

6. The implant of claim 1, characterized in that the sealing element, in the decompressed state, is a circular O ring and has a circular cross-section.

7. The implant of claim 1, characterized in that the sealing element is designed as a circular O ring and has an elongate cross-section.

8. The implant of claim 7, characterized in that the elongate cross-section is an elliptical cross-section.

\* \* \* \* \*